US010881470B2

(12) United States Patent
Falardeau et al.

(10) Patent No.: US 10,881,470 B2
(45) Date of Patent: Jan. 5, 2021

(54) METHOD AND DEVICE FOR CUP IMPLANTING USING INERTIAL SENSORS

(71) Applicant: ORTHOSOFT INC., Montreal (CA)

(72) Inventors: Bruno Falardeau, Verdun (CA); Karine Duval, Montreal (CA); Yvan Leone, Montreal (CA); Francois Paradis, Boucherville (CA); Di Li, Lasalle (CA); Myriam Valin, Laval (CA); Benoit Pelletier, Laval (CA); Laurence Moreau-Belanger, Laval (CA)

(73) Assignee: ORTHOSOFT ULC, Montreal (CA)

( * ) Notice: Subject to any disclaimer, the term of this patent is extended or adjusted under 35 U.S.C. 154(b) by 402 days.

(21) Appl. No.: 15/013,507

(22) Filed: Feb. 2, 2016

(65) Prior Publication Data
US 2016/0220318 A1 Aug. 4, 2016

Related U.S. Application Data

(60) Provisional application No. 62/110,850, filed on Feb. 2, 2015.

(51) Int. Cl.
*A61B 34/30* (2016.01)
*A61B 34/10* (2016.01)
(Continued)

(52) U.S. Cl.
CPC .............. *A61B 34/30* (2016.02); *A61B 34/10* (2016.02); *A61B 34/20* (2016.02); *A61B 34/70* (2016.02);
(Continued)

(58) Field of Classification Search
CPC .. A61B 2034/2048; A61B 34/20; A61B 34/30
See application file for complete search history.

(56) References Cited

U.S. PATENT DOCUMENTS 8,974,468 B2   3/2015  Borja
9,649,160 B2   5/2017  van der Walt et al.
(Continued)

FOREIGN PATENT DOCUMENTS

CN   103735303 A    4/2014
WO   2012010366 A1  1/2012
(Continued)

*Primary Examiner* — Olivia C Chang
(74) *Attorney, Agent, or Firm* — Norton Rose Fulbright Canada LLP

(57) ABSTRACT

A computer-assisted surgery (CAS) system comprises a cup implanting device including a shaft having a tooling end and a handle end with a handle for being manipulated, the shaft having a longitudinal axis, the tooling end adapted to support a cup for being received in an acetabulum of a patient, and a rotation indicator having a visual guide representative of a device plane, wherein the device plane is in a known position and orientation relative to a center of the cup on the tooling end. A CAS processing unit includes at least one inertial sensor unit connected to the cup implanting device, the inertial sensor unit outputting three-axes readings and having a virtual preset orientation related to a reference axis of a pelvis of the patient, the virtual preset orientation being based on pre-operative imaging specific to the pelvis of the patient, the reference axis of the pelvis passing through a center of rotation of said acetabulum of the pelvis and through a reference landmark of the pelvis, wherein an instant three-axis orientation of the longitudinal axis of the cup implanting device is trigonometrically known relatively to the reference axis when the cup is in the acetabulum of the patient and the device plane passes through the reference landmark via the visual guide, the instant three-axis orientation used for calibrating the inertial sensor unit on the cup implanting device relative to the pelvis.

18 Claims, 3 Drawing Sheets

(51) Int. Cl.
*A61B 34/00* (2016.01)
*A61B 34/20* (2016.01)
*A61B 17/16* (2006.01)

(52) U.S. Cl.
CPC ... *A61B 17/1666* (2013.01); *A61B 2034/2048* (2016.02); *A61B 2034/2055* (2016.02)

(56) References Cited

U.S. PATENT DOCUMENTS

| | | |
|---|---|---|
| 2005/0021044 A1 | 1/2005 | Stone et al. |
| 2010/0076505 A1 | 3/2010 | Borja |
| 2010/0249796 A1 | 9/2010 | Nycz |
| 2011/0184419 A1 | 7/2011 | Meridew et al. |
| 2014/0031722 A1 | 1/2014 | Li et al. |
| 2014/0052149 A1 | 2/2014 | van der Walt et al. |
| 2014/0364858 A1* | 12/2014 | Li .................. A61F 2/4609 606/91 |
| 2017/0296274 A1* | 10/2017 | van der Walt ........ A61F 2/4657 |

FOREIGN PATENT DOCUMENTS

| | | |
|---|---|---|
| WO | 2014063181 A1 | 5/2014 |
| WO | 2014071193 A1 | 5/2014 |

* cited by examiner

METHOD AND DEVICE FOR CUP IMPLANTING USING INERTIAL SENSORS

TECHNICAL FIELD

The present disclosure relates to a method and system for orienting an acetabular cup implant in computer-assisted surgery using inertial sensors.

BACKGROUND OF THE ART

In hip arthroplasty, the acetabulum is reamed to subsequently receive therein an acetabular cup (a.k.a., cup implant). The acetabular cup is an implant that is received in the reamed acetabulum and serves as a receptacle for a femoral head or femoral head implant. Accordingly, tools such as a reamer and a cup impactor are used in the procedure. One of the challenges in such procedures is to provide an adequate orientation to the acetabular cup. Indeed, an inaccurate orientation may result in a loss of movements, improper gait, and/or premature wear of implant components. For example, the acetabular cup is typically positioned in the reamed acetabulum by way of an impactor. The impactor has a stem at an end of which is the acetabular cup. The stem is handled by an operator that impacts the free end so as to drive the acetabular cup into the acetabulum. It is however important that the operator holds the stem of the impactor in a precise three-dimensional orientation so as to ensure the adequate orientation of the acetabular cup, in terms of inclination and anteversion.

For this purpose, computer-assisted surgery has been developed in order to help the operator in positioning and orienting the impactor to a desired orientation, notably by enabling the determination of the pelvic tilt, acetabular plane or like orientation data of the pelvis. Among the various tracking technologies used in computer-assisted surgery, optical navigation, C-arm validation and manual reference guides have been used. The optical navigation requires the use of a navigation system, which adds operative time. It also requires pinning a reference on the patient, which adds to the invasiveness of the procedure. It is also bound to line-of-sight constraints which hamper the normal surgical flow. C-arm validation requires the use of bulky equipment and the validation is not cost-effective. Moreover, it does not provide a quantitative assessment of the cup positioning once done, and is generally used post-operatively as opposed to intra-operatively. Finally, manual jigs, such as an A-frame, do not account for the position of the patient on the operative table. Accordingly, inertial sensors are used for their cost-effectiveness and the valuable information they provide.

SUMMARY

In accordance with a first embodiment of the present disclosure, there is provided a computer-assisted surgery (CAS) system comprising: a cup implanting device including a shaft having a tooling end and a handle end with a handle for being manipulated, the shaft having a longitudinal axis, the tooling end adapted to support a cup for being received in an acetabulum of a patient, and a rotation indicator having a visual guide representative of a device plane, wherein the device plane is in a known position and orientation relative to a center of the cup on the tooling end; and a CAS processing unit including at least one inertial sensor unit connected to the cup implanting device, the inertial sensor unit outputting three-axes readings and having a virtual preset orientation related to a reference axis of a pelvis of the patient, the virtual preset orientation being based on pre-operative imaging specific to the pelvis of the patient, the reference axis of the pelvis passing through a center of rotation of said acetabulum of the pelvis and through a reference landmark of the pelvis, wherein an instant three-axis orientation of the longitudinal axis of the cup implanting device is trigonometrically known relatively to the reference axis when the cup is in the acetabulum of the patient and the device plane passes through the reference landmark via the visual guide, the instant three-axis orientation used for calibrating the inertial sensor unit on the cup implanting device relative to the pelvis.

Further in accordance with the first embodiment, the center of the cup on the tooling end, the longitudinal axis and the visual guide commonly lie in the device plane, and wherein the instant three-axis orientation of the longitudinal axis of the cup implanting device is known relatively to the reference axis when the cup is in the acetabulum of the patient and the device plane passes through the reference axis via the visual guide.

Still further in accordance with the first embodiment, the visual guide is a light source and the device plane is a planar light beam.

Still further in accordance with the first embodiment, a receptacle is in the body for releasably receiving the inertial sensor unit.

Still further in accordance with the first embodiment, the preset virtual orientation of the inertial sensor unit comprises the reference axis passing through an anterior-superior iliac spine as the reference landmark.

Still further in accordance with the first embodiment, two of said at least one inertial sensor unit are provided, one of said inertial sensor unit being connected to the cup implanting device, another one of said inertial sensor unit incorporated in a pelvic reference adapted to be fixed to the pelvis of the patient, for tracking the reference axis during movements of the pelvis.

Still further in accordance with the first embodiment, the inertial sensor unit includes a virtual pelvic orientation representative of a current operative condition.

Still further in accordance with the first embodiment, the virtual pelvic orientation comprises a tilt of a medio-lateral axis of the patient.

Still further in accordance with the first embodiment, the virtual preset orientation is for the patient being in supine decubitus.

In accordance with a second embodiment of the present disclosure, there is provided a method for determining an orientation of a cup implanting device relative to a pelvis, with an inertial sensor unit in computer-assisted surgery comprising: obtaining a virtual preset orientation based on pre-operative imaging specific to a pelvis of a patient, the virtual preset orientation being related to a reference axis of a pelvis of the patient, the reference axis including a center of rotation of the acetabulum and a reference landmark; with a cup at an end of the cup implanting device in the acetabulum of the patient, obtaining orientation readings about two axes for the cup implanting device, relative to the pelvis, from the inertial sensor unit; with a device plane of the cup implanting device visually aligned with the reference landmark, determining an instant position of the device plane relative to the pelvis by using a geometric relation of the device plane relative to the cup implanting device and the orientation readings; trigonometrically calculating an instant three-axis orientation of the cup implanting device relative to the pelvis, using the instant position of the device plane; and calibrating the inertial sensor unit on the cup implanting device relative to the pelvis using the instant three-axis orientation.

Further in accordance with the second embodiment, further comprising obtaining an orientation of the medio-lateral axis of the patient, and wherein determining the instant position comprises.

Still further in accordance with the second embodiment, wherein obtaining an orientation of the medio-lateral axis of the patient comprises obtaining the orientation from an inertial sensor unit secured to the pelvis.

Still further in accordance with the second embodiment, wherein obtaining an orientation of the medio-lateral axis of the patient comprises obtaining the orientation from manipulations performed with the inertial sensor unit prior to being attached to the cup implanting device.

Still further in accordance with the second embodiment, further comprising tracking the orientation of the cup implanting device in three degrees of freedom relative to the pelvis.

Still further in accordance with the second embodiment, wherein tracking the orientation of the cup implanting device relative to the pelvis comprises outputting an anteversion and an inclination of the cup.

Still further in accordance with the second embodiment, wherein the virtual preset orientation is for the patient being in supine decubitus, and further wherein obtaining orientation readings about two axes for the cup implanting device, relative to the pelvis, from the inertial sensor unit comprises obtaining orientation readings representative to an angle between a longitudinal axis of the cup implanting device and a ground plane, and representative of a rotation of the cup implanting device about its longitudinal axis.

In accordance with a third embodiment of the present disclosure, there is provided a method for calculating an orientation of a cup implanting device relative to a pelvis using inertial sensors, comprising: obtaining pelvic tilt data; with a cup implanting device holding a cup in the acetabulum and pointing to a reference landmark, determining the initial orientation of the cup implanting device using the pelvic data, inertial sensor readings and pre-planned cup implanting device data; as the cup implanting device moves, tracking movements of the cup implanting device using inertial sensor readings; and calculating and outputting orientation data for the cup relative to the pelvic tilt data for the tracked movements of the cup implanting device using the pre-planned cup implanting device data.

DETAILED DESCRIPTION

Figure 1:
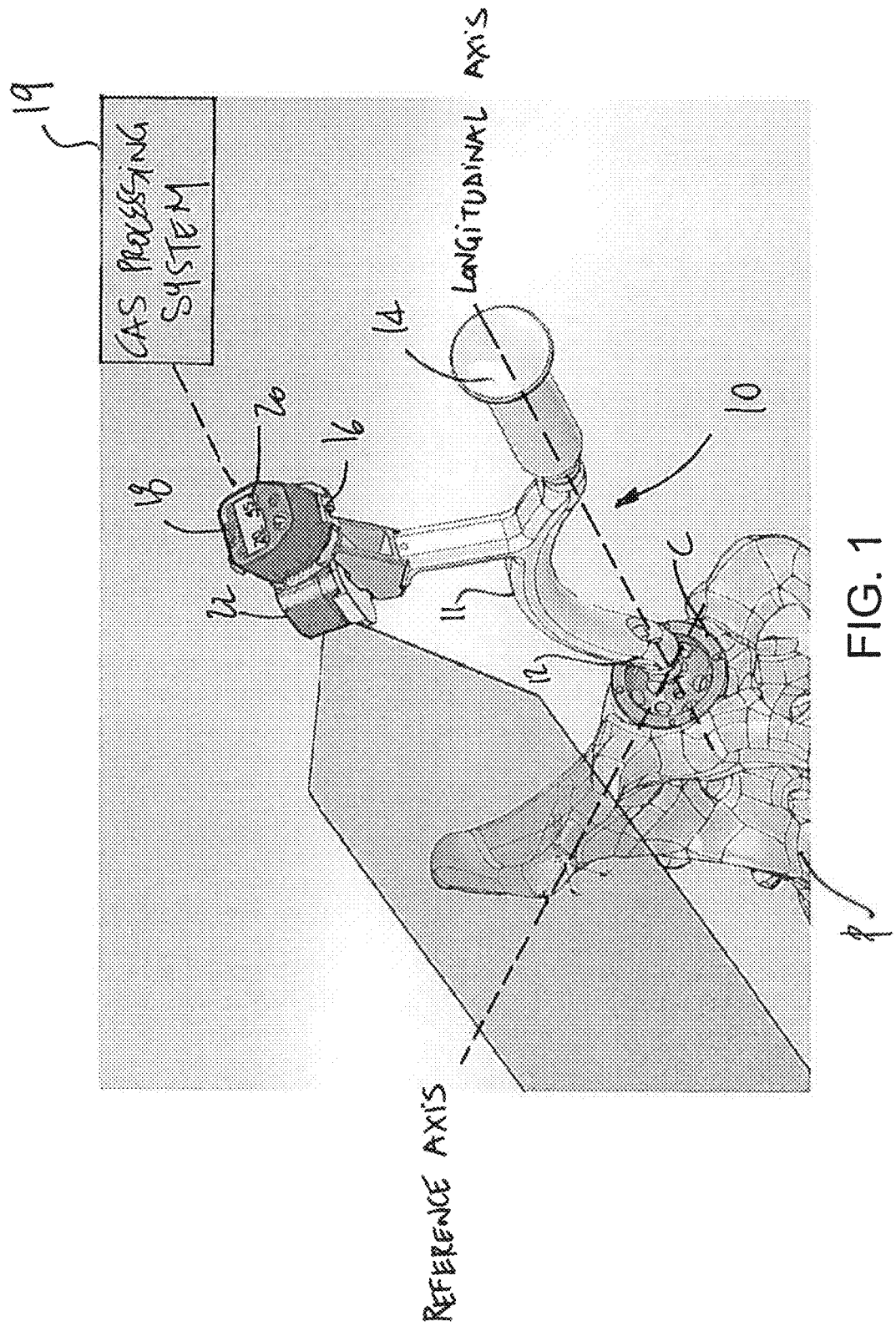
FIG. 1 is a perspective view of acetabulum cup impactor device with a cup relative to a pelvis.

Referring to the drawings and more particularly to FIG. 1, an acetabulum cup impactor device (a.k.a., implanting device, pelvic digitizer) is generally shown at 10, relative to a pelvis P having an acetabulum A. The device 10 and method related to the device 10 may be used to determine orientation data in various forms (e.g., anteversion/inclination of acetabulum or acetabular cup during implanting procedure, etc). In particular, the device 10 and method include the calibration (a.k.a., registration) required for inertial sensors of the device 10 to subsequently be tracked (a.k.a., navigated) relative to the orientation of the pelvis.

The device 10 is similar in its form and function to a cup impactor used in standard total hip arthroplasty. Alternatively, the device 10 may have some of its components part of a kit which mounts to a single position and orientation onto already existing impactors.

The device 10 has an elongated body 11 (i.e., stem or shaft) having a tooling end 12 and an impact end 14 (free end). Although illustrated as having an axially offset portion, the body of the device 10 may also be fully straight or have any other appropriate shape. The illustrated shape is however convenient for manipulations. An acetabular cup implant C is connected to the tooling end 12 in any appropriate manner (e.g., threading engagement, quick coupling, mating engagement), however in such a way that the implant C remains connected to the tooling end 12 during impacting, the device 10 then being disconnected from the implant C post impaction.

The device 10 may have a receptacle 16 for releasably receiving therein an inertial sensor unit 18, in a known manner. Alternatively, the inertial sensor unit 18 may be integral or embedded into the elongated body 11. The inertial sensor unit 18 contains at least two MEMS sensors (i.e., microelectromechanical systems), such as an accelerometer set and a gyroscope set which are oriented in a fixed and known orientation relatively to the longitudinal axis of the device 10, for instance with initialization virtual axes of the MEMS sensors aligned with landmarks of the device 10, such as the elongated body 11. Other types of inertial sensors may be provided in the inertial sensor unit 18 to complement the data or as alternatives to the accelerometer and/or gyroscope, such as inclinometers, magnetometers, among other possible inertial sensors and/or MEMS.

The inertial sensor unit 18 is part of a computer-assisted hip surgery system for navigating instruments, used to implement the method 10, as will be detailed below. The system comprises a computer-assisted surgery (CAS) processing unit 19 that may be a stand-alone computer connected to the inertial sensor unit 18, by wired or wireless communication. It is however pointed out that the CAS processing unit may be partially or integrally integrated into the inertial sensor unit 18 (a.k.a., pod) or one of the inertial sensor units when more than one is used. The inertial sensor unit 18, when incorporating the CAS processing unit, may thus be equipped with user interfaces 20 to provide the navigation data, whether it be in the form of LED displays, screens, numerical displays, etc. However, as the computer-assisted hip surgery system described herein may use more than one of the inertial sensor units, it is considered to have a stand-alone CAS processing unit 19 to receive data from all inertial sensors 18 and give the operator centralized guidance. This may also include local guidance by having data indicators on the inertial sensor units 18, such as anteversion and offset indicator lights or displays on the inertial sensor unit 18 of the device 10, as shown in FIG. 1.

For context, the inertial sensor unit 18 uses inertial sensor readings to continually calculate the orientation and velocity of a body without the need for an external reference. This process is commonly known and documented as dead reckoning and forms part of the common general knowledge. An initial orientation and velocity must be provided to the inertial sensor unit 18, i.e., the X-Y-Z coordinate system of FIG. 1, after which the orientation is tracked by integrating the angular rates of gyroscope readings at each time step. With an accurate estimate of the orientation of the inertial sensor unit 18 with respect to the World frame of reference, gravitational effects can be removed and inertial forces acting on the accelerometer sets can be integrated to track changes in velocity and position. Since the inertial sensor unit 18 has no need for an external reference, it may be immune to environmental factors such as magnetic fields and operate under a wide range of conditions.

The device 10 may additionally comprise a rotation indicator 22 (a.k.a., pointing device), used to acquire a missing third degree of freedom, rotation about the yaw axis, as described hereinafter. The rotation indicator 22 is positioned at a fixed position and orientation relative to the center of the acetabular cup C, when attached to the tooling end 12 of the device 10. In the illustrated embodiment, the rotation indicator 22 is a light source, such as a planar laser which projects a line onto a surface, or a laser beam producing a point. In the case of a planar laser, the line is representative of a known orientation when projected onto a reference landmark, and is thus used when defining the initial position of the device 10 as described hereinafter. In an embodiment, the longitudinal axis of the device 10 lies in the light plane produced by the rotation indicator 22. In an alternative embodiment, a distance and vector of the light plane is known relative to the center of the acetabular cup C.

In another embodiment, the rotation indicator 22 may be a mechanical arm which would point towards the reference landmark when defining the initial position of the device 10. In yet another embodiment, the rotation indicator 22 may be a visor through which the operator would aim for a reference landmark when defining the initial position of the device 10.

The CAS processing unit 19 may be programmed with virtual geometric data relating the body 11 (e.g., its axes) and the rotation indicator 22 to the virtual coordinate system of the inertial sensor unit 18. This virtual geometric data is programmed into the CAS processing unit 19 and is used to perform the method and sequence described below. For instance, a pre-operative planning step may be required to identify anatomical landmarks such as pelvis or patient coordinate system, an expected acetabulum cup center, a reference landmark for subsequent use of the rotation indicator 22 in pointing to it, and a relation between patient landmarks and a medio-lateral axis of the patient. This pre-operative planning may be performed using various imaging techniques, such as CT-scan reconstruction, 3D imaging techniques or reconstruction of the landmarks by using two X-Ray images, among other methods.

Figure 2:
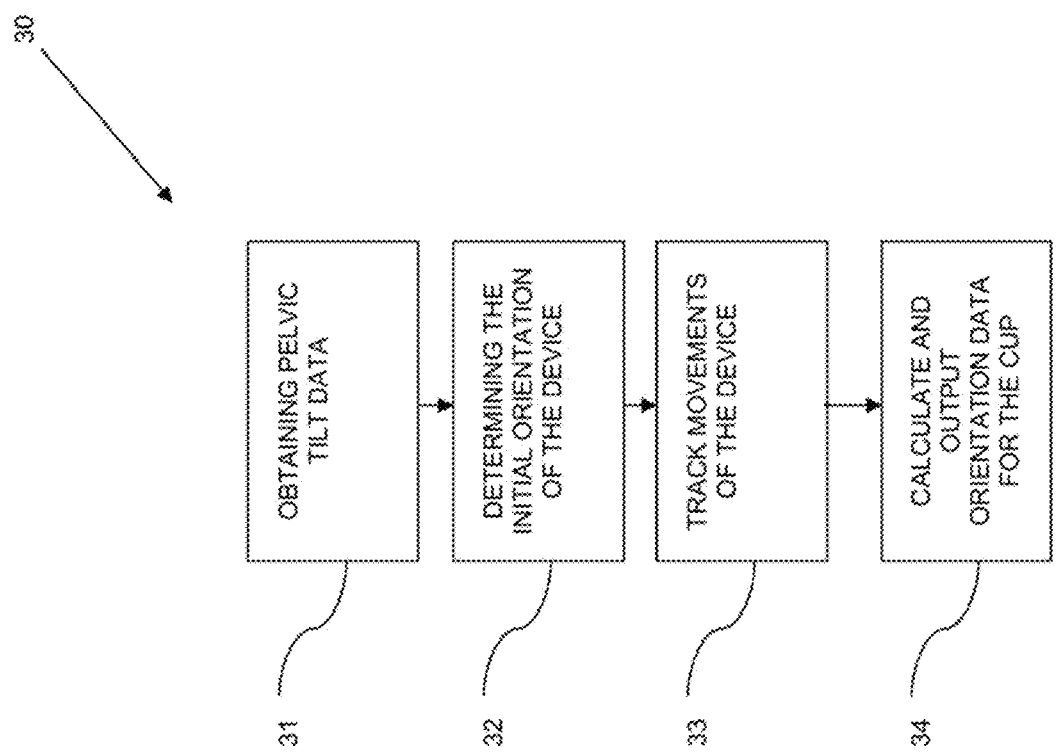
FIG. 2 is a flow chart of a method for calculating an orientation of a cup implanting device relative to a pelvis using inertial sensors.

Referring to FIG. 2, there is illustrated a method 30 for orienting an impactor, such as the device 10, relative to a pelvis for subsequently impacting an impactor cup C into the acetabulum of the pelvis P, in a desired relative orientation. In order to orient the impactor, a virtual frame of reference must be created, referred to as World coordinate system.

According to an embodiment, the patient may be positioned in supine decubitus. In supine decubitus, the World coordinate system (World) is defined with the following convention:

Z-Axis is aligned with the gravity vector;
X-Axis is aligned with the medio-lateral axis of the patient projected on the ground plane (e.g., OR table); and
Y-Axis is the cross product of vectors of the Z-Axis and X-Axis.

The method 30 described hereinafter may require obtaining at 31 the current tilt (both antero-posterior and lateral/inferior-superior) of the pelvis P, in World. This can be achieved using various existing and documented techniques. For instance, a patient-specific jig may be used on the acetabulum to record the current tilt or to position a reference inertial sensor on the patient, as described in PCT international publication no. WO 2014/197988, incorporated herein by reference. As another possibility, an acetabulum rim digitizer device (application Ser. No. 62/110,872) may be used to record the current tilt. As yet another possibility, a caliper instrument may be used to record the current tilt or position a reference on the pelvis for instance as per US Patent Application Publication No. 2014/0031829, incorporated herein by reference.

Hence, known techniques and instruments, some of which are publicly disclosed, may be used to provide the pelvic tilt to the method 30 and to the inertial sensor unit 18 of the device 10.

If the patient is in lateral decubitus, the patient can be positioned on the table such that his/her medio-lateral axis is aligned with the gravity axis. In supine decubitus, the patient can be positioned on the table such that his/her antero-posterior plane is aligned with the table/perpendicular to the gravity axis. In both cases, if the physical positioning of the pelvis is such that an operator is satisfied that the pelvis is substantially aligned with gravity (i.e., the medio-lateral axis aligned with the gravity axis for lateral decubitus, the anterior-posterior axis aligned with the gravity axis in supine decubitus), the step 31 of obtaining the current tilt may not be necessary.

In an embodiment, an additional inertial sensor unit (hereinafter, the pelvic reference) may be fixed onto the pelvis, such that the tilt of the patient can be tracked throughout the steps of method 10 once obtained in 31, and hence pelvic motion would be allowed. In the embodiments where no fixed pelvic reference is provided, it is assumed that the pelvis does not move during the method 10 all the way to the impaction of the cup C, whereby pelvic motion must be physically prevented or limited.

According to an embodiment, the pelvic reference is a pod similar to the one shown on the device 10 in FIG. 1. With the patient on the operating room table (e.g., seated), or standing prior to laying on the operating room table, the pelvic reference is adhered to the back of the patient. The pelvic reference may be fixed in such a way that one of the axes of the pelvic reference is aligned with the lateral plane (a.k.a., sagittal plane) of the patient, although other arrangements are considered as well. The location of the pelvic reference can be over the posterior superior iliac spine, slightly above it or below it. The means of fixation of the pelvic reference may include double-face tape, Ioban™ or any other material with suitable adherence.

In this defining of the pelvic tilt in World with the patient in a supine position, an assumption may be made that the patient's longitudinal axis matches the ground plane (i.e. the plane perpendicular to gravity). As mentioned previously, the caliper instrument, for instance that of US Patent Application Publication No. 2014/0031829, having another inertial sensor pod fixed to it, may be used to register the lateral tilt of the pelvis. With the assumption of the longitudinal axis matching the ground plane, the lateral tilt is sufficient to provide a definition of the pelvis coordinate system in World: the rotation of the medio-lateral axis of the pelvis about the Y axis of World. Such an assumption of the longitudinal axis matching the ground plane is not necessary when pelvic reference is in the back of the patient, whereby the pelvic coordinate system in World is trackable via the pelvic reference and thus tracking the lateral tilt. Although the present disclosure relates to cup impactor navigation, the use of an adhered pelvis pelvic reference may be used to track the pelvis in other applications, such as acetabular reaming, guiding pin place, placement, etc. However, the method and device 10 may achieve the navigation of the cup impaction without the back reference.

In an embodiment, after obtaining the pelvic tilt in 31, the inertial sensor unit 18 may be taken from the caliper instrument and be inserted in the receptacle 16 of the device 10, using dead reckoning to follow this unattached movement and bring the pelvic coordinate system in World to the device 10.

Referring to FIG. 2, the method 30 comprises determining an initial orientation of the device 10, at 32, to calibrate or register the device 10 in World. The orientation of the device 10 is qualified by three different attributes, i.e., three rotational degrees of freedom:

Pitch: the angle between the longitudinal axis of the device 10, or cup normal, and a plane perpendicular to the gravity vector (i.e., in which the X-Axis and the Y-Axis lie). This information is known and provided by the accelerometer set of the inertial sensor unit 18.

Roll: This is the rotation of the device 10 about its longitudinal axis. This information is known and provided by the accelerometer set of the inertial sensor unit 18.

Yaw: This is the rotation of the device 10 about the gravity vector (i.e., the Z-Axis). This value is not initially provided by the accelerometer set, and step 32 determines the yaw using pitch and roll, to calibrate (a.k.a., register) the device 10 for subsequent navigation of its orientation relative to the pelvis.

A null of known reference yaw is assumed for a reference axis passing through the acetabulum center (or acetabulum cup center) and a reference landmark. The pre-operative planning is used to define and program in the CAS processing unit 19 this reference axis passing between the acetabulum center and the reference landmark in the pelvic coordinate system. In an embodiment, the reference axis passes through the acetabulum center and the anterior-superior iliac spine, due to its visual distinctiveness to the human eye. Other reference landmarks may be used as well.

Moreover, according to an embodiment, by convention, the origin of World is positioned at the acetabulum center, which acetabulum center can be identified in imaging during the pre-operative planning, and which acetabulum center is a position that is attained by the device 10 when the cup C is in the acetabulum A. The pelvic coordinate system (via step 31), the acetabulum center, the reference landmark (both identifiable in the pre-operative imaging) and thus the reference axis are positioned in World.

The accelerometer set of the inertial sensor unit 18 provides two degrees of freedom (roll and pitch) for the orientation of the device 10. The position of the device 10 is also known as the cup C at the tooling end 12 has its center coincident with the acetabulum center. The only missing degree of freedom is the yaw of the device 10. It is possible to identify the yaw of the device 10 from the following settings and constraints, with the device 10 having the acetabular implant C received in the acetabulum such that the center of the cup C at the tooling end 12 is coincident with the acetabulum center:

The pelvic orientation in World is known, due to strict patient positioning or due to the acquiring of the pelvic coordinate system as detailed above in 31;

The virtual position of the reference axis in World is known, as pre-planned and as related to the pelvic coordinate system;

Pitch and roll of the device 10 are provided by the accelerometer set of the inertial sensor unit 18;

The rotation indicator 22 is oriented to point the reference landmark;

The geometric relation is known between the rotation indicator 22 and the acetabular implant C, as programmed into the inertial sensor unit 18.

There is only a single orientation of the device 10 in which all of the above constraints and settings apply. More particularly, the orientation of the plane incorporating the light beam of the rotation indicator 22 and the longitudinal axis of the device 10 is known through pre-programming of the inertial sensor unit 18. When this device plane passes through both the acetabulum center and the reference landmark, the position of the plane becomes known using the pitch and roll of the device 10, i.e., it passes through the reference axis, already known in World. Using the known position of the plane in World, the calculation of the instant yaw is straightforward trigonometry.

In an embodiment, the device plane does not pass through the acetabulum center, but the offset and orientation between the device plane and the acetabulum center is known, as part of the geometric relation between the rotation indicator 22 and the acetabular implant. In this case, when this device plane passes through the reference landmark, using the pitch and roll of the device 10, the position of the plane becomes known. Using the the known position of the plane in World, the calculation of the instant yaw is straightforward trigonometry.

Once yaw is calculated, this instant initial orientation in three axes is set by the inertial sensor unit 18 of the CAS processing unit 19, and becomes a navigation parameter tracked by the CAS processing unit 19. Hence, because of the recordation of the instant yaw, the device 10 is trackable in three axes in World, and thus relative to the pelvic coordinate system, previously defined in World.

Determining the initial orientation of the device 10 at 32 may be done without using preoperative planning. This alternate approach assumes a strict method of positioning the pelvis, according to which the pelvic medio-lateral axis is parallel to the gravity vector. Following this assumption, the user is required to position the device 10 according to the following constraints:

The rotation indicator 22, preferably a planar laser, points towards two landmarks on the medio-lateral axis, typically both pelvic anterior superior iliac spines; and The longitudinal axis of the device 10 is positioned in the patient transverse plane.

From these two constraints, knowing that the pitch and roll of the device 10 are provided by the accelerometer set in the inertial sensor unit 18, only a single orientation relatively to the pelvis is possible, i.e., the calculation of the instant yaw is straightforward trigonometry. This initial orientation is recorded by the CAS processing unit 19 and used in navigation.

Referring to FIG. 2, at 33, the orientation of the device 10 is tracked in three axes following the determination of the initial orientation of 32.

Once the initial orientation of the device 10 has been determined in 32, it is possible to track the orientation of the device 10 in three axes of World without further using the rotation indicator 22. The angular velocity provided by the gyroscope set in inertial sensor unit 18 is integrated over time to track the orientation of the device 10 in space using dead reckoning. In embodiments where a pelvic reference is attached to the pelvis, gyroscope readings thereof can also be used to track any subsequent motion of the pelvis. Tracking both pelvis and device 10 allows the calculation of their relative orientation in space and from this, clinical angles such as anteversion and inclination of the cup C, may be calculated. In the absence of a pelvic reference on the pelvis, the tracking of the device 10 used with the pelvic tilt is sufficient to determine anteversion and inclination of the cup C as the pelvic is kept immobile.

Hence, at step 34, orientation data for the cup C is calculated and output by the CAS processing unit (e.g., using the user interface on the inertial sensor unit 18) for the tracked movements of the device 10 as set forth above, using the pelvic coordinate system defined in World along with the three-axes tracking of the device 10.

Therefore, according to the method 30, an impactor such as the device 10, is programmed with geometric data specific to the patient landmarks in a pre-operative planning phase, for subsequent use in its steps. According to 31, pelvic tilt is obtained, for instance by performing registration of the current pelvic tilt, and this may entail positioning a reference onto the pelvis to track pelvic tilt after registration. According to 32, an initial orientation of the device 10 is determined. With the cup C secured to the device 10, the cup C is positioned into the reamed acetabulum A. Without removing the cup C from the acetabulum A, the rotation indicator 22 of the device 10 is pointed towards the reference landmark. With the device 10 seating the cup C into the acetabulum, and the rotation indicator 22 oriented towards the reference landmark, the user performs an input to record the initial orientation and indicate the beginning of the navigation. According to 33, an orientation of the device 10 is tracked in space. If a pelvic reference is attached to the pelvis, pelvic movements are also tracked. The tracking of 33 is performed by a dead reckoning operation, using the data from the gyroscope in the inertial sensor unit 18 and the pelvic reference, if applicable. As the orientation of the device 10 changes, cup placement navigation angles or like data is calculated and displayed.

When the cup C is in the desired orientation, the device 10 is used to impact the cup C in the reamed acetabulum A. The navigation of instruments is intended to mean tracking at least some of the degrees of freedom of orientation in real-time or quasi-real time, such that the operator is provided with navigation data calculated by computer assistance. The World coordinate system is a virtual frame of reference that serves as a reference to quantify the relative orientation of the different items of the surgery, i.e., the instruments and devices relative to the pelvis.

Figure 3:
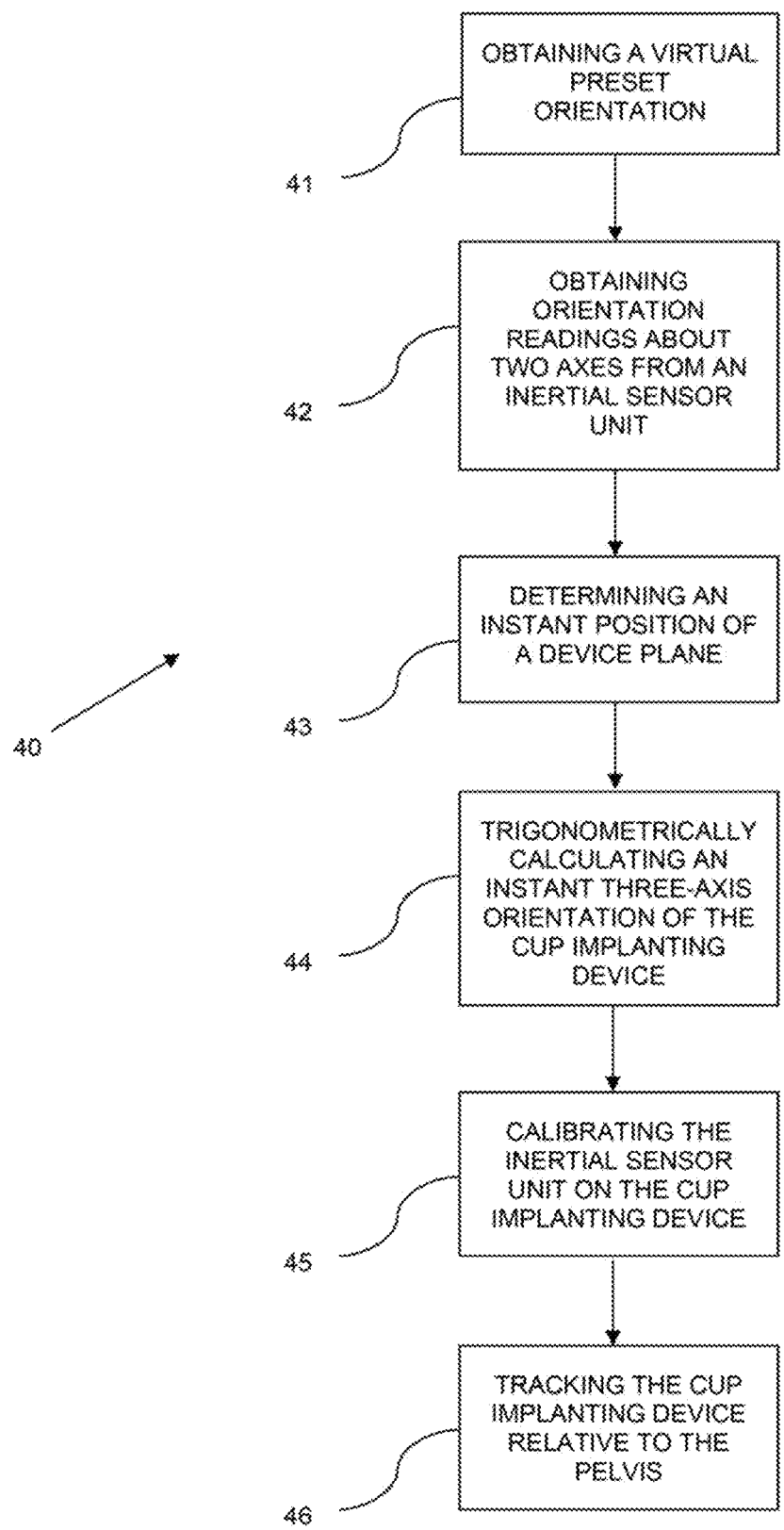
FIG. 3 is a flow chart of a method for determining an orientation of a cup implanting device relative to a pelvis, with an inertial sensor unit in computer-assisted surgery.

Referring to FIG. 3, there is illustrated a method 40 for determining an orientation of the cup implanting device 10 relative to a pelvis, from a perspective of the CAS processor system, such as the one incorporating the inertial sensor unit 18 and the CAS processing unit 19.

According to 41, a virtual preset orientation is obtained and is based on pre-operative imaging specific to a pelvis of a patient. The virtual preset orientation is programmed into the CAS processor system to be related to a reference axis of a pelvis of the patient, the reference axis including a center of rotation of the acetabulum and a reference landmark. The virtual preset orientation may be for the patient being in supine decubitus.

According to 42, with a cup at an end of the cup implanting device in the acetabulum of the patient, orientation readings about two axes (pitch and roll) for the cup implanting device 10 are obtained, relative to the pelvis, from the inertial sensor unit 18.

According to 43, with a device plane of the cup implanting device 10 visually aligned with the reference landmark, an instant position of the device plane relative to the pelvis is determined. To do so, a geometric relation of the device plane relative to the cup implanting device 10 is used, as well as and the orientation readings. The orientation of the medio-lateral axis of the patient may be used in the calculations.

According to 44, an instant three-axis orientation of the cup implanting device 10 relative to the pelvis is trigonometrically calculated, using the instant position of the device plane.

According to 45, the inertial sensor unit 18 on the cup implanting device 10 is calibrated relative to the pelvis using the instant three-axis orientation.

According to 46, the orientation of the cup implanting device 10 is tracked relative to the pelvis and in three degrees of freedom, and may be outputted as an anteversion and an inclination of the cup C.

The invention claimed is:

1. A computer-assisted surgery (CAS) system comprising:
a cup implanting device including
a shaft having a tooling end and a handle end with a handle for being manipulated, the shaft having a longitudinal axis, the tooling end adapted to support a cup for being received in an acetabulum of a patient, and
a rotation indicator having a visual guide representative of a device plane,
wherein the device plane is in a known position and orientation relative to a center of the cup on the tooling end; and
a CAS processing unit including at least one inertial sensor unit connected to the cup implanting device, the inertial sensor unit configured to output three-axes readings, the CAS processing unit configured to: obtain a virtual preset orientation for the inertial sensor unit, the virtual preset orientation including a planned trigonometric relation with a reference axis of a pelvis of the patient, the virtual preset orientation being based on pre-operative imaging specific to the pelvis of the patient, the reference axis of the pelvis passing through a center of rotation of said acetabulum of the pelvis and through a reference landmark of the pelvis; trigonometrically calculate an instant three-axis orientation of the longitudinal axis of the cup implanting device relative to the reference axis when the cup is in the acetabulum of the patient and the device plane passes through the reference landmark via the visual guide; calibrate the inertial sensor unit on the cup implanting device relative to the pelvis using the instant three-axis orientation.

2. The CAS system according to claim 1, wherein the center of the cup on the tooling end, the longitudinal axis and the visual guide commonly lie in the device plane, and wherein the instant three-axis orientation of the longitudinal axis of the cup implanting device is known relative to the reference axis when the cup is in the acetabulum of the patient and the device plane passes through the reference axis via the visual guide.

3. The CAS system according to claim 1, wherein the visual guide is a light source and the device plane is a planar light beam.

4. The CAS system according to claim 1, further comprising a receptacle in the cup implanting device for releasably receiving the inertial sensor unit.

5. The CAS system according to claim 1, wherein the preset virtual orientation of the inertial sensor unit comprises the reference axis passing through an anterior-superior iliac spine as the reference landmark.

6. The CAS system according to claim 1, comprising two of said at least one inertial sensor unit, one of said inertial sensor unit being connected to the cup implanting device, another one of said inertial sensor unit incorporated in a pelvic reference adapted to be fixed to the pelvis of the patient, for tracking the reference axis during movements of the pelvis.

7. The CAS system according to claim 1, wherein the at least one inertial sensor unit includes a virtual pelvic orientation representative of a current operative condition.

8. The CAS system according to claim 7, wherein the virtual pelvic orientation comprises a tilt of a medio-lateral axis of the patient.

9. The CAS system according to claim 1, wherein the virtual preset orientation is for the patient being in supine decubitus.

10. A computer-assisted surgery (CAS) system comprising:
   a cup implanting device including
      a shaft having a tooling end and a handle end with a handle for being manipulated, the shaft having a longitudinal axis, the tooling end adapted to support a cup for being received in an acetabulum of a patient, and
      a rotation indicator having a visual guide representative of a device plane, the visual guide being a light source producing a single light beam,
      wherein the device plane is in a known position and orientation relative to a center of the cup on the tooling end; and
   a CAS processing unit including at least one inertial sensor unit connected to the cup implanting device, the inertial sensor unit configured to output three-axes readings, the CAS processing unit configured to: obtain a virtual preset orientation for the inertial sensor unit, the virtual preset orientation including a planned trigonometric relation with a reference axis of a pelvis of the patient, the virtual preset orientation being based on pre-operative imaging specific to the pelvis of the patient, the reference axis of the pelvis passing through a center of rotation of said acetabulum of the pelvis and through a reference landmark of the pelvis; trigonometrically calculate an instant three-axis orientation of the longitudinal axis of the cup implanting device relative to the reference axis when the cup is in the acetabulum of the patient and the single light beam passes through the reference landmark; calibrate the inertial sensor unit on the cup implanting device relative to the pelvis using the instant three-axis orientation.

11. The CAS system according to claim 10, wherein the center of the cup on the tooling end, the longitudinal axis and the visual guide commonly lie in the device plane, and wherein the instant three-axis orientation of the longitudinal axis of the cup implanting device is known relative to the reference axis when the cup is in the acetabulum of the patient and the device plane passes through the reference axis via the visual guide.

12. The CAS system according to claim 10, wherein the single light beam is a planar light beam.

13. The CAS system according to claim 10, further comprising a receptacle in the cup implanting device for releasably receiving the inertial sensor unit.

14. The CAS system according to claim 10, wherein the preset virtual orientation of the inertial sensor unit comprises the reference axis passing through an anterior-superior iliac spine as the reference landmark.

15. The CAS system according to claim 10, comprising two of said at least one inertial sensor unit, one of said inertial sensor unit being connected to the cup implanting device, another one of said inertial sensor unit incorporated in a pelvic reference adapted to be fixed to the pelvis of the patient, for tracking the reference axis during movements of the pelvis.

16. The CAS system according to claim 10, wherein the inertial sensor unit includes a virtual pelvic orientation representative of a current operative condition.

17. The CAS system according to claim 16, wherein the virtual pelvic orientation comprises a tilt of a medio-lateral axis of the patient.

18. The CAS system according to claim 10, wherein the virtual preset orientation is for the patient being in supine decubitus.

* * * * *